(12) United States Patent
Fields

(10) Patent No.: US 6,247,996 B1
(45) Date of Patent: Jun. 19, 2001

(54) BREAST MILK PUMP SUPPORT HARNESS

(76) Inventor: Angel Fields, 3943 Millstream Ct., Lawrenceville, GA (US) 30044

( * ) Notice: Subject to any disclaimer, the term of this patent is extended or adjusted under 35 U.S.C. 154(b) by 0 days.

(21) Appl. No.: 09/604,886

(22) Filed: Jun. 26, 2000

(51) Int. Cl.$^7$ .................................................. A41C 3/10

(52) U.S. Cl. .............................................. 450/36; 450/37

(58) Field of Search ........................... 450/36, 37; 2/104; 604/73–76; 601/14, 6; 128/890; 54/20, 58, 59

(56) References Cited

U.S. PATENT DOCUMENTS

| 1,509,226 | 9/1924 | Brown . |
| 1,670,610 | 5/1928 | Colby . |
| 3,782,385 | 1/1974 | Loyd ...................................... 128/281 |
| 5,049,126 | 9/1991 | Larsson ................................... 604/74 |
| 5,514,166 | 5/1996 | Silver et al. ........................... 604/74 |
| 5,575,768 | 11/1996 | Lockridge et al. .................... 607/74 |
| 5,616,125 | 4/1997 | Jelks ...................................... 604/74 |

Primary Examiner—Gloria M. Hale
(74) Attorney, Agent, or Firm—Joseph N. Breaux

(57) ABSTRACT

A breast milk pump support harness to be worn by a nursing mother that includes two detachable collection bottle support assemblies and a brassiere assembly.

1 Claim, 3 Drawing Sheets

BREAST MILK PUMP SUPPORT HARNESS

TECHNICAL FIELD

The present invention relates to breast milk pumps and the like and more particularly to a breast milk pump support harness that includes two detachable collection bottle support assemblies and a brassiere assembly; the brassiere assembly including two push-up breast support cups, two breast cover flaps—each securable over a respective push-up breast support cup, four collection bottle attachment fasteners—two positioned adjacent each push-up breast support cups, and four collection bottle attachment straps—two positioned on either side of each of the push-up breast support cups; each breast support cup including a V-shaped, nipple access opening; each of the detachable collection bottle support assemblies including a pair of brassiere fastener sections that companionately attach to two of the four collection bottle attachment fasteners.

BACKGROUND ART

It is often difficult and time consuming to use a breast milk pump because the user must support the breast milk pump in position against the breast. It would be desirable, therefore, to have a breast milk pump support harness that included a mechanism for securing a breast milk pump in place in a manner such that there is no need for the user to hold the breast milk pump in position against the breast during use.

GENERAL SUMMARY DISCUSSION OF INVENTION

It is thus an object of the invention to provide a breast milk pump support harness that includes two detachable collection bottle support assemblies and a brassiere assembly; the brassiere assembly including two push-up breast support cups, two breast cover flaps—each securable over a respective push-up breast support cup, four collection bottle attachment fasteners—two positioned adjacent each push-up breast support cups, and four collection bottle attachment straps—two positioned on either side of each of the push-up breast support cups; each breast support cup including a V-shaped, nipple access opening; each of the detachable collection bottle support assemblies including a pair of brassiere fastener sections that companionately attach to two of the four collection bottle attachment fasteners.

Accordingly, a breast milk pump support harness is provided. The breast milk pump support harness includes two detachable collection bottle support assemblies and a brassiere assembly; the brassiere assembly including two push-up breast support cups, two breast cover flaps—each securable over a respective push-up breast support cup, four collection bottle attachment fasteners—two positioned adjacent each push-up breast support cups, and four collection bottle attachment straps—two positioned on either side of each of the push-up breast support cups; each breast support cup including a V-shaped, nipple access opening; each of the detachable collection bottle support assemblies including a pair of brassiere fastener sections that companionately attach to two of the four collection bottle attachment fasteners.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

EXEMPLARY MODE FOR CARRYING OUT THE INVENTION

Figure 1:
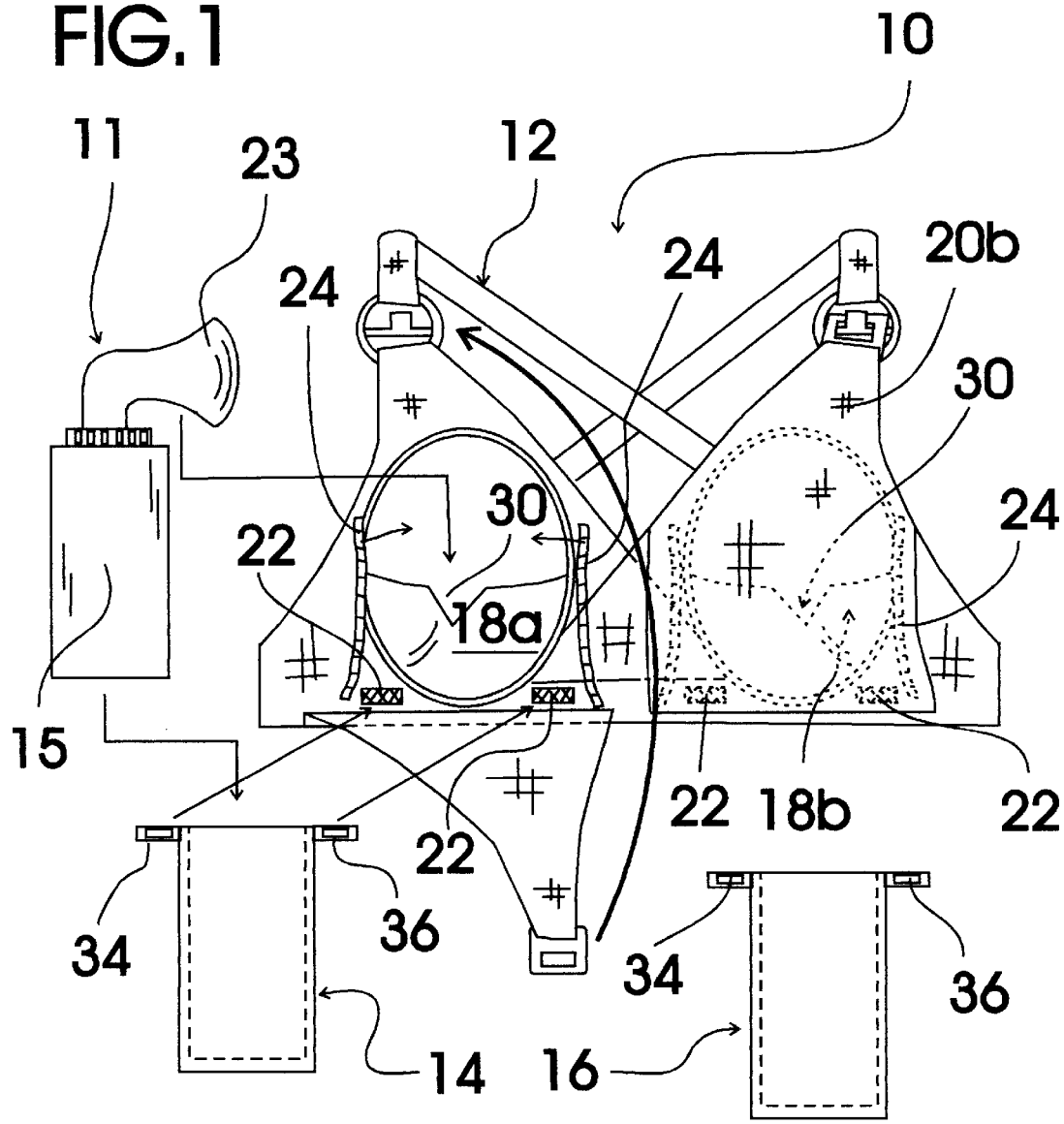
FIG. 1 is a front perspective view of an exemplary embodiment of the breast milk pump support harness of the present invention and a representative breast milk pump assembly.
Figure 2:
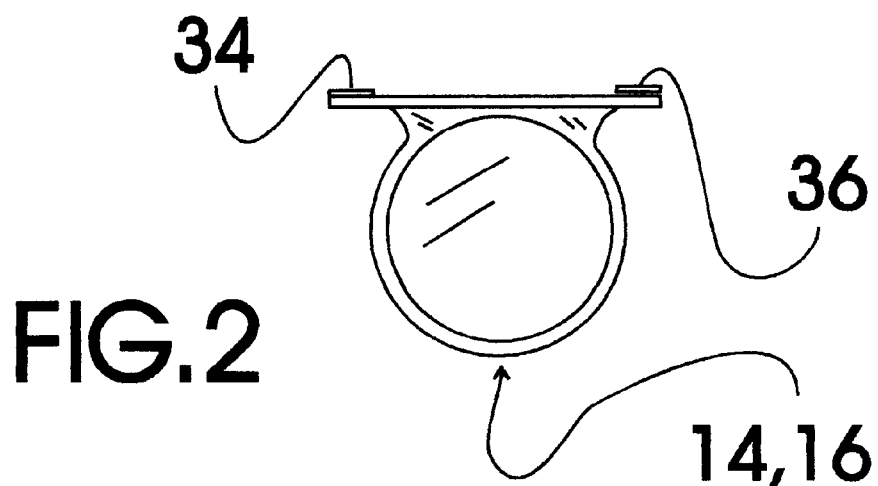
FIG. 2 is a top plan view showing one of the two identical detachable collection bottle support assemblies.
Figure 3:
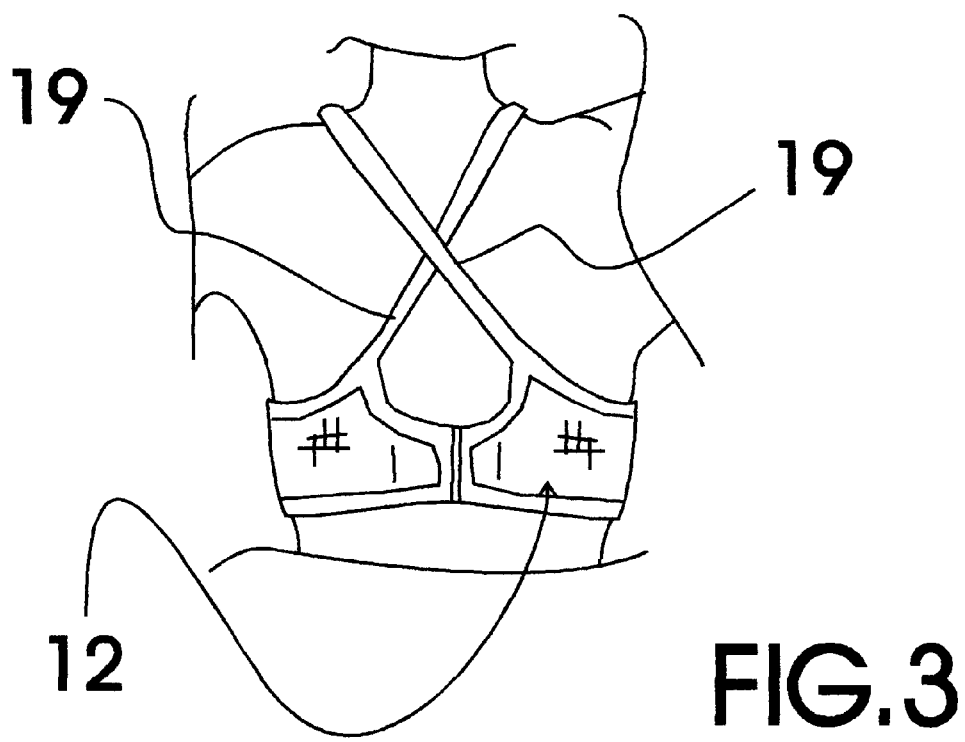
FIG. 3 is a back plan view of the back of the brassiere assembly.

FIGS. 1–2 shows various aspects of an exemplary embodiment of the breast milk pump support harness of the present invention, generally designated 10, adapted for use with a breast milk pump 11 including a collecting bottle 13 and a collection bottle portion 15 and a nipple cover member 23.

Breast milk pump support harness 10 includes two identical, detachable collection bottle support assemblies, generally designated 14,16 and a brassiere assembly, generally designated 12.

Figure 4:
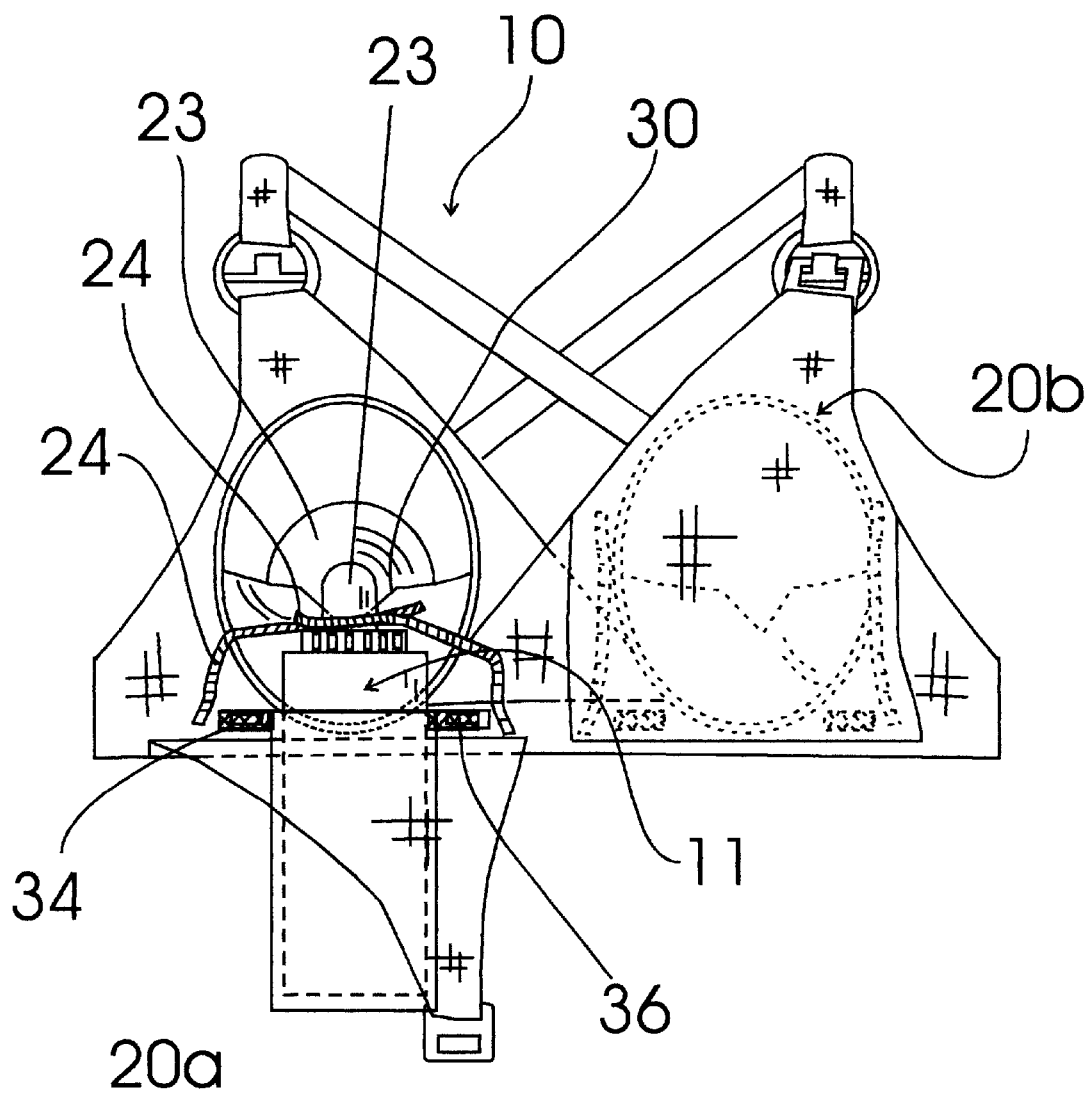
FIG. 4 is a front plan view showing the collection bottle portion of the representative breast milk pump assembly installed in connection with one of the two detachable collection bottle support assemblies.

Brassiere assembly 12 includes two back straps 19 two push-up breast support cups, generally designated 18a,18b, (18b shown in dashed lines) two breast cover flaps, generally designated 20a,20b —each securable over a respective push-up breast support cup 18a,18b; four collection bottle attachment fasteners, generally designated 22,—two positioned adjacent each push-up breast support cups 18a,18b (the two collection bottle attachment fasteners of support cup 18b are shown in dashed lines) - - - ; and four collection bottle attachment straps 24—two positioned on either side of each of the push-up breast support cups 18a,18b(the two collection bottle attachment straps 24 of support cup 18b are shown in dashed lines) - - - ;. Each breast support cup 18a,18b includes a V-shaped, nipple access opening 30. Each of the detachable collection bottle support assemblies 14,16 including a pair of brassiere fastener sections 34,36 (both shown in dashed lines in FIG. 1) - - - ; that companionately attach to two of the four collection bottle attachment fasteners 22 and a bottle cavity 27. Once a detachable collection bottle support assembly 14,16 is attached as just described; the bottom portion of collection bottle 13 is positioned into bottle cavity 27 and nipple cover member 23 is placed in V-shaped notch 30; the two collection bottle attachment straps are then wrapped around nipple cover member 23 and attached to each other, as shown in FIG. 4, to secure nipple cover member securely over a women's nipple such that the breast milk pump 11 is supported while in operation.

It can be seen from the preceding description that a breast milk pump support harness has been provided.

It is noted that the embodiment of the breast milk pump support harness described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A breast milk pump support harness comprising:

two detachable collection bottle support assemblies; and a brassiere assembly;

said brassiere assembly including two push-up breast support cups, two breast cover flaps—each securable over a respective push-up breast support cup, four collection bottle attachment fasteners—two positioned adjacent each push-up breast support cups, and four collection bottle attachment straps—two positioned on either side of each of said push-up breast support cups;

each breast support cup including a V-shaped, nipple access opening;

each of said detachable collection bottle support assemblies including a pair of brassiere fastener sections that companionately attach to two of said four collection bottle attachment fasteners.

* * * * *